(12) United States Patent
van Dijk (10) Patent No.: US 9,352,153 B2
(45) Date of Patent: May 31, 2016

(54) SYSTEMS AND METHODS FOR DETECTING NERVE STIMULATION WITH AN IMPLANTED PROSTHESIS

(75) Inventor: Bastiaan van Dijk, Mechelen (BE)

(73) Assignee: Cochlear Limited, Macquarie University, NSW (AU)

( * ) Notice: Subject to any disclaimer, the term of this patent is extended or adjusted under 35 U.S.C. 154(b) by 561 days.

(21) Appl. No.: 13/012,639

(22) Filed: Jan. 24, 2011

(65) Prior Publication Data

US 2012/0191161 A1    Jul. 26, 2012

(51) Int. Cl.
*A61N 1/36* (2006.01)
*A61N 1/05* (2006.01)

(52) U.S. Cl.
CPC .......... *A61N 1/36032* (2013.01); *A61N 1/0541* (2013.01); *A61N 1/36135* (2013.01)

(58) Field of Classification Search
CPC .......... A61N 1/36135; A61N 1/36032; A61N 1/0541; A61B 5/04001; A61B 5/7217; A61F 2/72
USPC .......................................................... 607/57
See application file for complete search history.

(56) References Cited

U.S. PATENT DOCUMENTS

| | | | |
|---|---|---|---|
| 5,626,629 A * | 5/1997 | Faltys et al. ...................... | 607/57 |
| 6,094,598 A | 7/2000 | Elsberry et al. | |
| 6,157,861 A | 12/2000 | Faltys et al. | |
| 6,208,882 B1 | 3/2001 | Lenarz et al. | |
| 6,415,185 B1 * | 7/2002 | Maltan ............................. | 607/57 |
| 6,915,166 B1 | 7/2005 | Stecker et al. | |
| 7,801,617 B2 | 9/2010 | Dijk | |
| 2005/0246004 A1 | 11/2005 | Cameron et al. | |
| 2005/0261748 A1 | 11/2005 | van Dijk | |
| 2006/0116737 A1 * | 6/2006 | Libbus ............................ | 607/44 |
| 2006/0235332 A1 | 10/2006 | Smoorenburg | |
| 2007/0142874 A1 | 6/2007 | John | |
| 2007/0255344 A1 | 11/2007 | van Dijk | |
| 2008/0319508 A1 * | 12/2008 | Botros et al. .................... | 607/57 |
| 2009/0054946 A1 | 2/2009 | Sommer et al. | |
| 2009/0306743 A1 | 12/2009 | Van Den Heuvel | |
| 2010/0121416 A1 * | 5/2010 | Lee ................................. | 607/66 |

(Continued)

FOREIGN PATENT DOCUMENTS

| CN | 101081188 A | 12/2007 |
|---|---|---|
| WO | 2008031169 A1 | 3/2008 |

(Continued)

OTHER PUBLICATIONS

International Search Report for Application PCT/IB2012/000086 mailed Sep. 19, 2012 (8 pages).
Office Action with English Translation in counterpart Chinese Application No. 201280006266.6, dated Apr. 3, 2015, 19 pages.
English Translation of Office Action in counterpart Chinese Application No. 201280006266.6, dated Nov. 4, 2015, 4 pages.

*Primary Examiner* — Christopher D Koharski
*Assistant Examiner* — Jeremiah Kimball (57) ABSTRACT

The present application discloses systems and methods for detecting non-auditory nerve stimulation with an implant having a plurality of electrodes configured to electrically stimulate a target nerve of the implant recipient. One embodiment includes generating an electrical stimulation signal with a first set of electrodes of the implant, measuring a response to the electrical stimulation signal with a second set of electrodes of the implant, and determining whether the electrical stimulation signal stimulated at least one non-target nerve of the implant recipient based on the measured response.

26 Claims, 8 Drawing Sheets

(56) References Cited

U.S. PATENT DOCUMENTS

| | | | |
|---|---|---|---|
| 2010/0125304 A1* | 5/2010 | Faltys | 607/2 |
| 2010/0161005 A1* | 6/2010 | Wahlgren et al. | 607/62 |
| 2010/0228317 A1 | 9/2010 | Libbus et al. | |
| 2011/0015700 A1 | 1/2011 | Dijk | |
| 2012/0143284 A1* | 6/2012 | Capcelea et al. | 607/57 |
| 2012/0158095 A1* | 6/2012 | Jolly | 607/57 |

FOREIGN PATENT DOCUMENTS

| | | |
|---|---|---|
| WO | 2009025916 A2 | 2/2009 |
| WO | 2009/026625 A1 | 3/2009 |
| WO | 2009076721 A1 | 6/2009 |

\* cited by examiner

SYSTEMS AND METHODS FOR DETECTING NERVE STIMULATION WITH AN IMPLANTED PROSTHESIS

BACKGROUND

Cochlear implants may provide a person having sensorineural hearing loss with the ability to perceive sound by stimulating the person's auditory nerve via an array of electrodes implanted in the person's cochlea. An external component of the cochlear implant detects sound waves, which are converted into a series of electrical impulses delivered to the implant recipient's auditory nerve via the array of electrodes. Stimulating the auditory nerve in this manner may enable the cochlear implant recipient's brain to perceive a hearing sensation that is similar to the natural hearing sensation delivered to the auditory nerve.

One problem with cochlear implants is that the electrodes can sometimes stimulate more than just the cochlear implant recipient's auditory nerve. The implant recipient may not always recognize non-auditory nerve stimulations, or may not be able to indicate reliably (as in the case of small children or mentally disabled recipients), but over time, non-auditory nerve stimulations can be annoying or even painful to the implant recipient. The most common non-auditory nerve stimulation is stimulation of the facial nerve.

Typically, when a cochlear implant is being surgically implanted into a recipient, external sensors applied to the surface of the recipient's skin are used to detect facial nerve impulses. Facial nerve impulses are large and fairly easy to detect with external sensors. These external sensors let the surgeon know when the facial nerve is touched during the surgery where the cochlear implant is being implanted into the recipient.

After the cochlear implant has been implanted into the recipient, an audiologist or other similarly-trained specialist may fine-tune the settings of the cochlear implant. Sometimes, the implant recipient may even fine-tune certain settings of the cochlear implant themselves. This post-operative fine-tuning process is known as "fitting" the implant to the recipient. During the fitting process, the audiologist or the recipient may adjust the cochlear implant settings in a way that causes the cochlear implant to stimulate the facial nerve. And because the recipient may not always be able to initially recognize the facial nerve stimulation, or because the recipient may not always be able to give reliable feedback, the resulting implant configuration may cause facial nerve stimulation.

SUMMARY

The present application discloses systems and methods for detecting non-auditory nerve stimulation with a cochlear implant having a plurality of electrodes configured to electrically stimulate a cochlear implant recipient's auditory nerve.

A method according to one embodiment includes generating an electrical signal with a first set of two or more electrodes of the cochlear implant, and then measuring a response to the electrical signal with at least two electrodes of the cochlear implant. The method further includes determining whether the electrical signal stimulated a non-auditory nerve based on the measured response.

In some embodiments, the cochlear implant may determine whether the electric signal stimulated a non-auditory nerve. In other embodiments, a computing device communicatively coupled to the cochlear implant may determine whether the electric signal stimulated a non-auditory nerve based on a measurement made by the cochlear implant.

In some embodiments, a computing device communicatively coupled to the cochlear implant may alert the operator of the computing device that a non-auditory nerve stimulation has been detected. In some embodiments, the method may further include changing one or more configuration settings of the cochlear implant in response to determining whether the electrical signal stimulated at least one non-auditory nerve.

In the embodiments where the cochlear implant determines whether a particular electric signal stimulated a non-auditory nerve, the cochlear implant may change its configuration settings based on whether it has detected a non-auditory nerve stimulation. In the embodiments where a separate computing device determines whether a particular electric signal stimulated a non-auditory nerve, the computing device may instruct the cochlear implant to change its configuration settings based on the computing device determining whether a non-auditory nerve was stimulated by the electric signal.

In the embodiments that include changing one or more configuration settings of the cochlear implant in response to determining whether the electrical signal stimulated at least one non-auditory nerve, the steps of changing one or more configuration settings may include changing any of the amplitude, pulse width, and/or stimulation pulse rate of the electrical signal in response to determining that the electrical signal stimulated at least one non-auditory nerve.

The method may additionally include changing at least one or both of an active or reference electrode for a particular channel to one or more different electrodes in the plurality of electrodes of the cochlear implant in response to determining whether the electrical signal stimulated at least one non-auditory nerve. Such embodiments may also include disabling one or more active electrodes in response to determining whether the electrical signal stimulated at least one non-auditory nerve.

In some embodiments, measuring the response to the electrical signal may include measuring one or more signal characteristics of a response signal with at least two electrodes of the cochlear implant, where the one or more signal characteristics may be based on the signal voltage, amperage, impedance, frequency, and/or duration. And in some embodiments, determining whether the first electrical signal stimulated at least one non-auditory nerve may include analyzing the measured response with a recognition algorithm implemented in software, hardware, firmware, or any combination thereof.

DETAILED DESCRIPTION

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

1. Cochlear Implant Overview

Figure 1A:
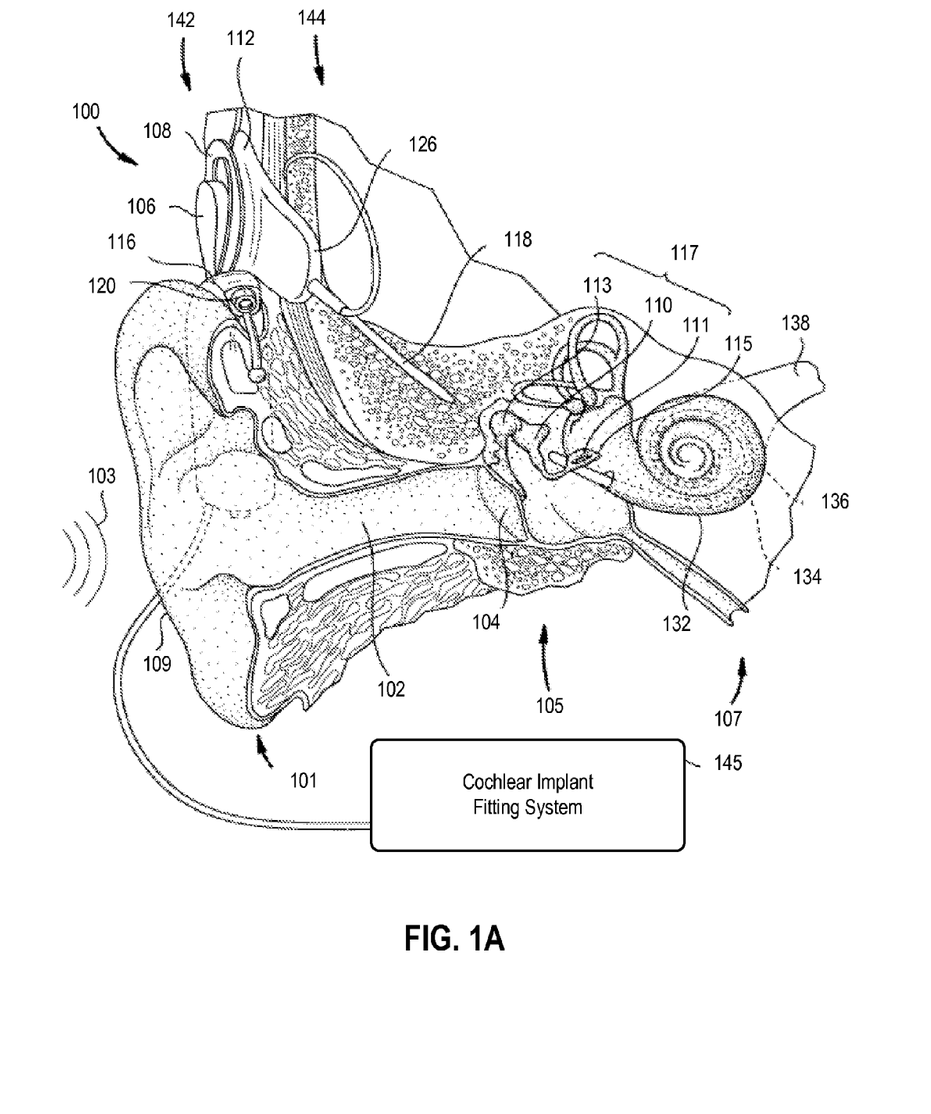
FIG. 1A shows one example embodiment of a cochlear implant that may be implanted into an implant recipient.

FIG. 1A shows a cochlear implant 100 implanted in a cochlear implant recipient. The relevant components of the recipient's outer ear 101, middle ear 105, and inner ear 107 are described herein, followed by a description of the cochlear implant 100.

For persons without certain types of hearing impairments, an acoustic pressure or sound wave 103 is collected by the auricle 109 and channeled into and through the ear canal 102. The tympanic membrane 104 is located at the distal end of the ear canal 102. The tympanic membrane 104 vibrates in response to the acoustic wave 103.

The vibration of the tympanic membrane 104 is coupled to the oval window or fenestra ovalis 115 through three bones of the middle ear 105, collectively referred to as the ossicles 117, and including the malleus 113, the incus 110, and the stapes 111. For persons without certain types of hearing impairments, the bones 113, 109 and 111 of the middle ear 105 serve to filter and amplify the acoustic wave 103, causing the oval window 115 to articulate and/or vibrate. The vibration of the oval window 115 causes waves of fluid motion within the cochlea 132. This fluid motion within the cochlea 132, in turn, activates tiny hair cells (not shown) that line the inside of the cochlea 132. Activation of the hair cells inside the cochlea 132 causes nerve impulses to be transferred through the spiral ganglion cells (not shown) and the auditory nerve 138 to the brain (not shown), where the nerve impulses are perceived as sound. But for persons with sensorineural hearing loss, a cochlear implant may instead be used to electrically stimulate the auditory nerve.

The cochlear implant 100 may include an external component assembly 142 that is directly or indirectly attached to the body of the recipient, and an internal component assembly 144 that is temporarily or permanently implanted in the recipient.

The external assembly 142 may include a sound processing unit 116 and an external transmitter unit 106. The sound processing unit 116 may include a digital signal processor (DSP), a power source to power the cochlear implant 100, and a sound transducer 120. The sound transducer 120 may be configured to detect sound and generate an audio signal, typically an analog audio signal, representative of the detected sound. In the example embodiment shown in FIG. 1A, the sound transducer 120 is a microphone. In alternative embodiments, the sound transducer 120 may comprise, for example, more than one microphone, one or more telecoil induction pickup coils, or other devices now or later developed that may detect sound and generate electrical signals representative of detected sound. In some embodiments, the sound transducer 120 may not be integrated into the sound processing unit 116, and may instead be a separate component of the external component assembly 142.

The external transmitter unit 106 may include an external coil 108 of a transcutaneous energy transfer system along with the associated circuitry to drive the coil. The external transmitter unit 106 may also preferably include a magnet (not shown) secured directly or indirectly to the external coil 108.

The sound processing unit 116 may be configured to process the output of the microphone 120 that is positioned, in the depicted embodiment, near the auricle 109 of the recipient. The sound processing unit 116 may be configured to generate coded signals, referred to herein as stimulation data signals, which can be provided to the external transmitter unit 106 via a cable (not shown). The sound processing unit 116 shown in this example embodiment is designed to fit behind the auricle 109. Alternative versions may be worn on or fully implanted in the body. Some fully implantable systems may incorporate the sound processing unit into the internal component assembly 144.

The internal component assembly 144 may include an internal receiver unit 112, a stimulator unit 126 and an electrode assembly 118. The internal receiver unit 112 and the stimulator unit 126 may be hermetically sealed within a biocompatible housing.

The internal receiver unit 112 may include an internal coil (not shown) of the noted transcutaneous transfer system, along with the associated circuitry. The implanted internal receiver unit 112 may be positioned in a recess of the temporal bone adjacent to the outer ear 101 of the recipient, as shown in FIG. 1A. The external coil 108 may be held in place and aligned with the implanted internal coil via the noted magnets. In one embodiment, the external coil 108 may be configured to transmit electrical signals to the internal coil via a radio frequency (RF) link.

The electrode assembly 118 may be designed to extend from the stimulator unit 126 to the cochlea 132 and to terminate in an array 134 of electrodes 136. Signals generated by the stimulator unit 126 are applied by the electrodes 136 to the cochlea 132, thereby stimulating the auditory nerve 138.

Further details of the above and other examples of cochlear implants that may be implemented in conjunction with embodiments of the disclosed systems and methods include, but are not limited to, those systems described in U.S. Pat. Nos. 4,532,930, 6,537,200, 6,565,503, 6,575,894 and 6,697,674, which are hereby incorporated by reference herein in their entireties.

As shown in FIG. 1A, the cochlear implant 100 is further configured to interoperate with a cochlear implant fitting system 145. The hearing implant fitting system 145 may be implemented with a computing device, such as a personal computer, workstation, handheld computing device, or the like. The fitting process is described in greater detail below with reference to an exemplary fitting environment illustrated in FIG. 1B.

2. Fitting System Overview

The effectiveness of the cochlear implant 100 depends not only on the device itself but also on how well the device is configured for or "fitted" to the recipient. The fitting of the cochlear implant, also referred to as "programming" or "mapping," creates a set of configuration settings and other data that defines the specific characteristics of the stimulation signals delivered to the electrodes 136 of the implanted array 134. This configuration information is referred to as the recipient's "program" or "MAP."

Figure 1B:
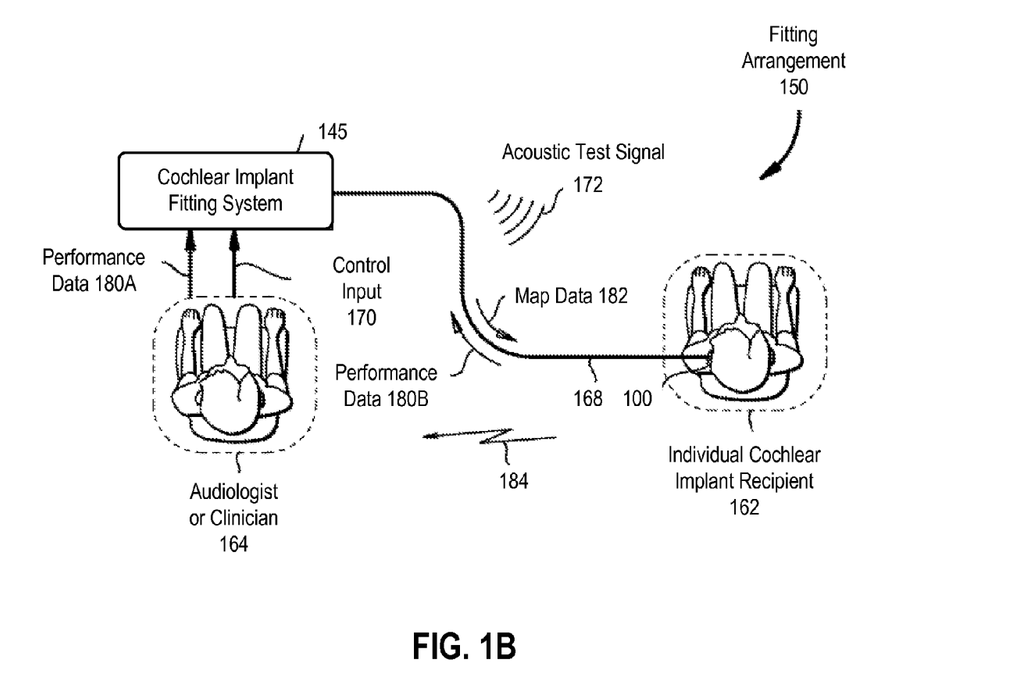
FIG. 1B shows an example of an audiologist or other similarly-trained clinician fitting a cochlear implant to an implant recipient.

FIG. 1B is a schematic diagram illustrating one example arrangement 150 where an audiologist or other clinician 164 uses the cochlear implant fitting system 145 to fit a cochlear implant 100 to a recipient 162. The cochlear implant fitting system 145 may include interactive software and computer hardware and/or firmware configured to create a recipient-specific implant configuration, shown as "map data" 182 in FIG. 1B. The map data 182 may be stored on the fitting system 145, and it also may be downloaded to the memory of the sound processing unit 116 (FIG. 1A) of the cochlear implant 100.

In the example shown in FIG. 1B, the sound processing unit 116 of the cochlear implant 100 may be communicatively coupled to the fitting system 145 to establish a data communication link 168 between the cochlear implant 100 and the fitting system 145. The fitting system 145 may thereafter be bi-directionally coupled to the cochlear implant 100 via the data communication link 168. Although the cochlear implant 100 and fitting system 145 are connected via a cable in FIG. 1B, any communications link now or later developed may be utilized to communicably couple these components, e.g., for example, a radio link or other communications link.

After the cochlear implant 100 has been implanted, specific map data 182 can be determined for the recipient. The particular details of the implemented fitting process may be specific to the recipient, cochlear implant manufacturer, cochlear implant device, etc. As a result, only selected example mapping data are described herein for clarity.

Currently, most cochlear implants may require at least two values to be set for each stimulating electrode of the array 134 of electrodes 136 of the cochlear implant 100. These values are referred to as the threshold level (commonly referred to as the "THR" or "T-level"; "threshold level" herein) and the Maximum Comfortable Loudness level (commonly referred to as the Most Comfortable Loudness level, "C-level"; "comfort level" herein). Threshold levels and comfort levels may vary from recipient to recipient and from stimulation channel to stimulation channel. The threshold levels and the comfort levels determine in part how well the recipient hears and understands detected speech and/or sound.

The threshold level may correspond to the level where the recipient first identifies sound sensation. In general, the threshold level is the lowest level of stimulation current that evokes the sensation of sound for a given channel. The threshold level can often be determined by passing the recipient's hearing threshold twice using an ascending method and determining the level at which the recipient experiences sound by observing their response, such as, for example, indicating gestures in the case of adults, or observing behavioral reactions in the case of children.

The comfort level may set the maximal allowable stimulation level for each electrode channel. The comfort level may correspond to the maximum stimulation current level that feels comfortable to the recipient. In setting and establishing the comfort levels, it may be usual for an audiologist or clinician to instruct the recipient to indicate a level that is "as loud as would be comfortable for long periods" while slowly increasing the stimulation for a particular channel. The comfort levels may affect how speech sounds to the recipient more than the threshold levels because most of the acoustic speech signal may generally be mapped onto approximately the top 20% of the threshold and comfort level range.

Although the terminology and abbreviations may be device-specific, the general purpose of threshold and comfort levels is to determine a recipient's electrical dynamic range by defining the lowest stimulation levels (threshold levels) and the highest acceptable stimulation levels (comfort levels) for each stimulation channel.

In adult cochlear implant recipients, the threshold and comfort levels may typically be set by using verbal feedback from the recipient 162. But for children who may lack the listening experience, language, and/or conceptual development to perform specific fitting tasks, audiologists and clinicians may need to rely on clinical intuition and trial and error to appropriately estimate comfort levels for younger recipients. The above and other feedback is generally referred to by reference numeral 184 in FIG. 1B. Performance data provided directly to fitting system 145 may be provided via data connection 168 as performance data 180B, while performance data provided by the audiologist/clinician based on oral feedback or observations 184 is shown in FIG. 1B as performance data 180A (performance data 180A and 180B are generally and collectively referred to as performance data 180).

3. Cochlear Implant Configuration and Operation

Figure 2A:
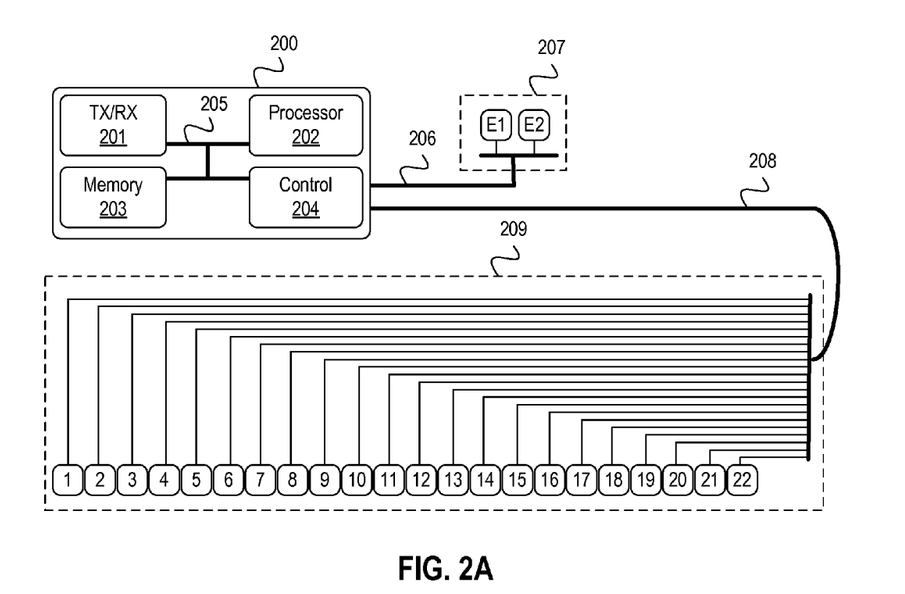
FIG. 2A shows a block diagram of certain selected cochlear implant components according to some embodiments of the disclosed systems and methods.

FIG. 2A shows a block diagram of a cochlear implant according to some example embodiments of the disclosed systems and methods. The cochlear implant 200 shown in FIG. 2A may have some or all of the components of cochlear implant 100 described in FIGS. 1A-B, but the configuration depicted in FIGS. 2A-B focuses on a selected set of components that may be helpful to illustrate certain aspects of the disclosed systems and embodiments.

In the example embodiment shown in FIG. 2A, cochlear implant 200 has a transmit/receive module 201, a processor module 202, a memory module 203, and a control module 204 that may be communicatively coupled to one or more communication links 205. In some embodiments, the transmit/receive module 201, the processor module 202, the memory module 203, and the control module 204 may be on a single integrated circuit. In other embodiments, the different modules may be on separate integrated circuits, and in other embodiments, two or more modules may be implemented on one integrated circuit while the remaining modules may be implemented on one or more different integrated circuits.

In some embodiments, the one or more communication links 205 may be a single shared communication link, such as a bus. In other embodiments, the one or more communication links 205 may include multiple dedicated links between the components of the cochlear implant 200 shown in FIG. 2A. For example, the one or more communication links 205 may include a dedicated link between the processor module 202 and the memory module 203, a dedicated link between the processor module 202 and the transmit/receive module 201, and a dedicated link between the processor module 202 and the control module 204. In other embodiments, some modules may be connected via shared links and other modules may be connected via dedicated links. Thus, the one or more communication links 205 may include any number of different shared and/or dedicated links between the various modules of the cochlear implant 200 shown in FIG. 2A.

The transmit/receive module 201 may be configured to communicatively couple the cochlear implant 200 to an external fitting system, such as fitting system 145 shown in FIGS. 1A and 1B. The transmit/receive module 201 may be configured to send and/or receive information to and/or from a fitting system. For example, in some embodiments, the transmit/receive module 201 may be configured to receive configuration or map data from a fitting system. The transmit/ receive module 201 may also be configured to send measurement data to a fitting system. In some embodiments, the transmit/receive module 201 may also be configured to send and/or receive data to/from other ancillary devices that may be associated with the cochlear implant 200.

The processor module 202 shown in FIG. 2A may include one or more processors, including but not limited to, programmable processors, application specific integrated circuits, programmable logic arrays, digital signal processors, and/or other general and/or special purpose processors configured to perform one or more of the functions of the cochlear implant 200 as described herein. For example, the one or more processors in the processor module 202 may be configured to encode external signals from a microphone (or other source) into stimulation signals for sending to the internal electrodes 209 of the cochlear implant via the connection 208. The one or more processors of the processor module 202 may also be configured to conduct one or more cochlear implant system diagnostic tests, analyze the results of the one or more cochlear implant system diagnostic tests, and/or implement one or more actions in response to the results of the one or more cochlear implant system diagnostic tests. In some embodiments, the one or more processors in the processor module 202 may also be configured to analyze measured responses to stimulation signals generated via the electrodes of the cochlear implant 200.

The memory module 203 shown in FIG. 2A may include one or more computer-readable storage media that can be read from, written to, or otherwise accessed by at least one processor of the processor module 202. In some embodiments, the storage media of the memory module 203 may also be read from, written to, or otherwise accessed by a fitting system, such as fitting system 145 (FIG. 1A). Additionally, the storage media of the memory module 203 may also be read from, written to, or otherwise accessed by one or more of the transmit/receive module 201 and/or the control module 204. In some embodiments, the storage media in the memory module 203 may be configured to store configuration, or MAP, data for the cochlear implant 200. The storage media of the memory module 203 may also be configured to store the results of one or more implant diagnostic tests that are initiated, performed, or otherwise controlled in part by either the one or more processors of the processor module 202 or a fitting system. In some embodiments, the storage media of the memory module 203 may also be configured to store measured responses to stimulation signals generated via the electrodes of the cochlear implant 200.

The cochlear implant 200 shown in FIG. 2A may also include a plurality of external electrodes 207 connected to the control module 204 of the cochlear implant 200 via connection 206 and a plurality of internal electrodes 209 connected to the control module 204 of the cochlear implant 200 via connection 208.

In the embodiment shown in FIG. 2A, the external electrodes 207 include electrodes E1 and E2. Other embodiments may have only one external electrode, while other embodiments may have more than two external electrodes. Still other embodiments may not have any external electrodes. The external electrodes may be located outside of the implant recipient's cochlea. In embodiments with two external electrodes, one of the external electrodes may be a ground electrode and one of the external electrodes may be a plate electrode.

In the embodiment shown in FIG. 2A, the internal electrodes 209 may include electrodes 1-22. Other embodiments may have more or fewer internal electrodes. In most embodiments, at least some of the internal electrodes 209 may be located inside an implant recipient's cochlea. In other embodiments, one or more of the internal electrodes 209 may be located outside of the implant recipient's cochlea. In some embodiments, one or more internal electrodes 209, sometimes together with one or more external electrodes 207, may be organized into individual sets of active and reference electrodes corresponding to individual stimulation channels. The stimulation channels can be configured to apply electrical signals to an implant recipient's cochlea. The organization and configuration of electrodes into stimulation channels is described in more detail herein.

2.1 Controlling Electrodes for Stimulation and Measurement

Figure 2B:
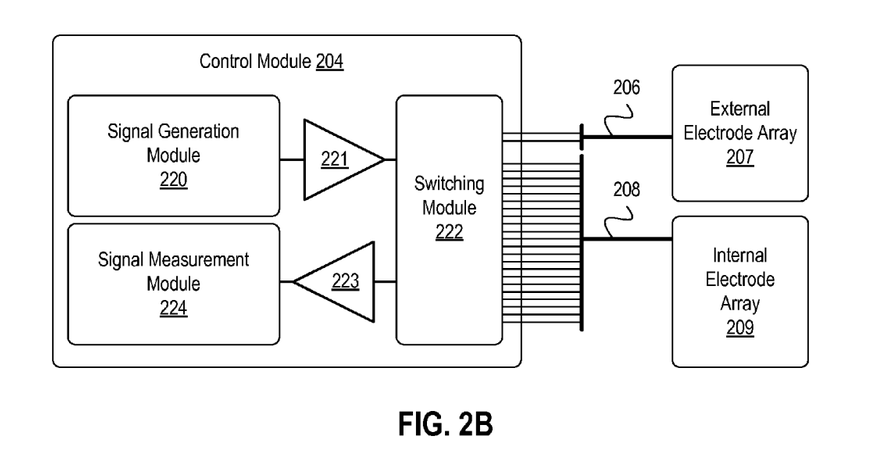
FIG. 2B shows a block diagram of an example control module of a cochlear implant according to some embodiments of the disclosed systems and methods.

The control module 204 shown in FIG. 2A may include circuitry configured to control and manage the internal electrodes 209 and the external electrodes 207. FIG. 2B shows a block diagram of one example control module 204 of a cochlear implant according to some embodiments of the disclosed systems and methods. The control module 204 shown in FIG. 2B is for illustrative purposes only, and the internal electrodes 209 and external electrodes 207 of the cochlear implant 200 may be managed and controlled via similar structures and elements configured to perform the functions described herein.

The block diagram of the example control module 204 shown in FIG. 2B may include a signal generation module 220, a transmit amplifier module 221, a switching module 222, a receive amplifier module 223, and a signal measurement module 224.

The signal generation module 220 may include circuitry configured to generate the electrical signals on the stimulation channels. Recall that encoding external signals from a microphone (or other source) into stimulation data signals for sending to the internal electrodes 209 of the cochlear implant via the connection 208 from the control module 204 may be one of the functions that the one or more processors of the processor module 202 may be configured to perform. In some embodiments, the signal generation module 220 may generate stimulation signals on particular stimulation channels based on the encoded data information determined by the one or more processors of the processor module 202.

Some embodiments of the control module 204 may also include a transmit amplifier module 221. The transmit amplifier module 221 may include one or more amplifiers that may be configured to control the stimulation signal levels on the stimulation channels so that signals stay substantially between the threshold levels and the comfort levels for the stimulation channels. In the embodiment shown in FIG. 2B, the transmit amplifier module 221 is shown before the switching module 222 in the signal chain from the signal generation module 220 to the electrodes, but in other embodiments, the transmit amplifier module 221 may be placed after the switching module 222. In still other embodiments, the transmit amplifier module 221 may be integrated into the signal generation module 220 or alternatively into the switching module 222.

The control module 204 shown in FIG. 2B may also include the switching module 222. The switching module 222 may include a plurality of signal switching mechanisms configured to control the activation and deactivation of the internal electrodes 209 and/or the external electrodes 207 and to control the signal path activation and deactivation of the stimulation channels. For example, in some of the systems and methods described herein, the switching mechanisms of the switching module 222 may be used to activate a specific stimulation channel to send an electrical stimulation signal from the signal generation module 220 to at least a portion of an implant recipient's cochlea for a defined duration, and to configure two or more electrodes to measure a response to the electrical stimulation signal. The switching mechanisms of the switching module 222 may also be used to disable one or more particular electrodes if the electrodes are determined to be defective, outside of their desired operating parameters, or otherwise causing an undesirable response by the implant recipient.

Some embodiments of the control module 204 may also include a receive amplifier module 223. The receive amplifier module 223 may include one or more amplifiers that may be configured to amplify a response signal measured by two or more electrodes of the cochlear implant 200. Amplifying a response signal measured by two or more electrodes of the cochlear implant 200 may make the response signal easier to analyze. In the embodiment shown in FIG. 2B, the receive amplifier module 223 is shown after switching module 222 in the signal chain from the electrodes to the signal measurement module 224, but in other embodiments, the receive amplifier module 223 may be placed before the switching module 222. In still other embodiments, the receive amplifier module 223 may be integrated into the signal measurement module 224 or alternatively into the switching module 222.

The control module 204 shown in FIG. 2B may also include the signal measurement module 224. The signal measurement module 224 may include circuitry configured to measure and/or analyze a signal received from the electrodes of the cochlear implant 200. In some embodiments, the signal measurement module 224 may be configured to store a copy of a measured signal into storage media of the memory module 203 for analysis by one or more processors of the processor module 202. Additionally, or alternatively, the signal measurement module 224 may also be configured to send a copy of a measured signal to the transmit/receive module 201 for sending to a fitting system and/or other external computing device for analysis. In still other embodiments, the signal measurement module 224 may additionally include circuitry and/or one or more processors configured to analyze a measured signal received from the electrodes from the cochlear implant 200.

2.2 Stimulation Modes for Stimulation Channels

An electrical stimulation generated by the cochlear implant may produce a flow of electrical current between at least one active electrode and at least one reference electrode. The set of the at least one active electrode and the at least one reference electrode corresponds to an individual stimulation channel. A cochlear implant may typically have multiple stimulation channels. Each stimulation channel may have a different set of active and reference electrodes. The stimulation mode of a particular stimulation channel describes the location of the one or more reference electrodes in relation to the at least one active electrode for the stimulation channel. The distance between the active and reference electrodes may determine the spread of the electrical current in the implant recipient's cochlea, and thus, the nerve endings or spiral ganglia that are stimulated by the electrical current of a particular stimulation channel.

Figure 3A:
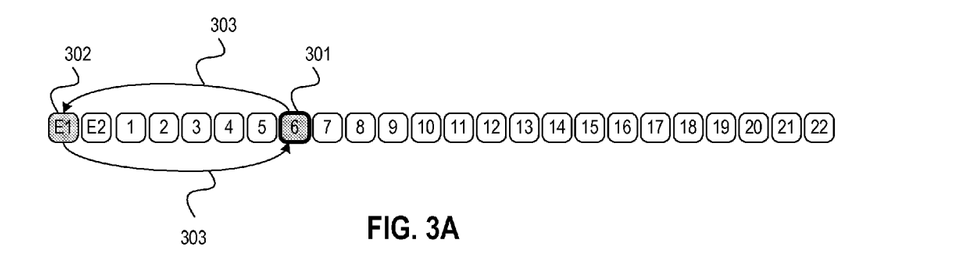
FIGS. 3A-3G show example channel configurations for generating an electrical signal with two or more electrodes of a cochlear implant according to some embodiments of the disclosed systems and methods.
Figure 3B:
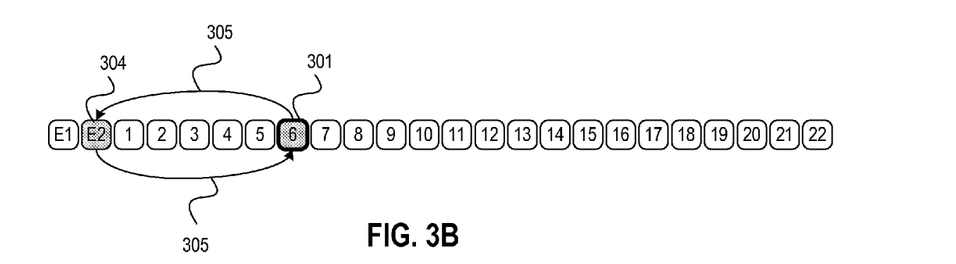

FIGS. 3A-3G show different examples of stimulation modes for stimulation channels. Each of FIGS. 3A-3B shows external electrodes E1 and E2 and internal electrodes 1-22 of a cochlear implant, such as cochlear implant 200 shown in FIG. 2A. Some cochlear implant embodiments may have only one external electrode, some cochlear implant embodiments may have no external electrodes, and some cochlear implant embodiments may have more than the two external electrodes shown in FIGS. 3A-3G. Similarly, some cochlear implant embodiments may have more or fewer than the twenty-two internal electrodes shown in FIGS. 3A-3G. The number of internal and external electrodes of a cochlear implant may determine the number of stimulation channels and the different types of stimulation modes that can be used by the cochlear implant.

Figure 3C:
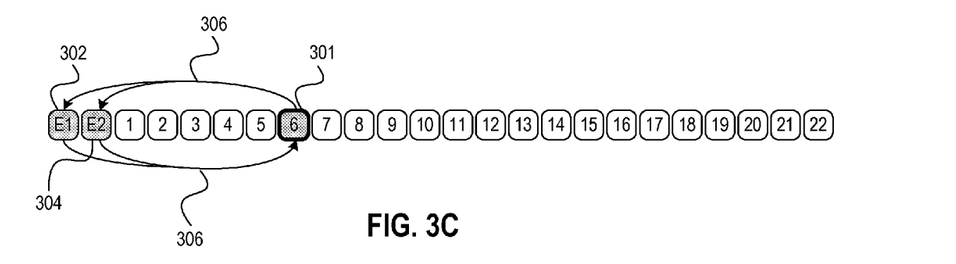

FIGS. 3A-3C show three examples of stimulation channels configured for different types of monopolar stimulation. In monopolar stimulation, the active electrode of the stimulation channel may be one of the internal electrodes, and the one or more reference electrodes may be one or more of the external electrodes. Monopolar stimulation may be used to produce the lowest threshold and comfort levels and may use less energy to produce electrical stimulation signals than other stimulation modes described herein. Monopolar stimulation may be used for stimulation signals with higher stimulation rates (i.e., higher frequency signals), such as signals encoded according to one or more of the Advanced Combination Encoder format, the Continuous Interleaved Sampling encoding format, and/or other encoding formats that use higher stimulation rate signals. In embodiments where one or more internal electrodes may be located outside of a patient's cochlea (e.g., situations where all the internal electrodes of the cochlear implant could not be implanted entirely inside the cochlea, for example), the one or more internal electrodes located outside of the implant patient's cochlea may be used as reference electrodes in the monopolar stimulation examples described herein.

FIG. 3A shows an example of a set of two electrodes configured for monopolar stimulation type 1 on a stimulation channel. For a stimulation channel configured for monopolar type 1 stimulation, current flows between an internal active electrode and an external reference electrode. In the example shown in FIG. 3A, the stimulation channel includes active electrode 301 and reference electrode 302, where the active electrode 301 corresponds to internal electrode 6, and the reference electrode 302 corresponds to external electrode E1. External electrode E1 may correspond to a ground electrode of the cochlear implant. When the stimulation channel of FIG. 3A is activated, current flows between the active electrode 301 and the reference electrode 302 via path 303.

FIG. 3B shows an example of a set of two electrodes configured for monopolar stimulation type 2 on a stimulation channel. For a stimulation channel configured for monopolar type 2 stimulation, current flows between an internal active electrode and an external reference electrode. In the example shown in FIG. 3B, the stimulation channel includes active electrode 301 and reference electrode 304, where the active electrode 301 corresponds to internal electrode 6, and the reference electrode 304 corresponds to external electrode E2. The external electrode E2 may correspond to a plate electrode of the cochlear implant. When the stimulation channel of FIG. 3B is activated, current flows between the active electrode 301 and the reference electrode 304 via path 305.

FIG. 3C shows an example of a set of three electrodes configured for monopolar stimulation type 1+2 on a stimulation channel. For a stimulation channel configured for monopolar type 1+2 stimulation, current flows between an internal active electrode and two external reference electrodes. In the example shown in FIG. 3C, the stimulation channel includes active electrode 301 and reference electrodes 302 and 304, where the active electrode 301 corresponds to internal electrode 6, and the external electrodes 302 and 304 correspond to external electrodes E1 and E2, respectively. External electrodes E1 and E2 may correspond to a ground electrode and a plate electrode of the cochlear implant, respectively. When the stimulation channel of FIG.

3C is activated, current flows between the active electrode 301 and the reference electrodes 302 and 304 via path 306.

Figure 3D:
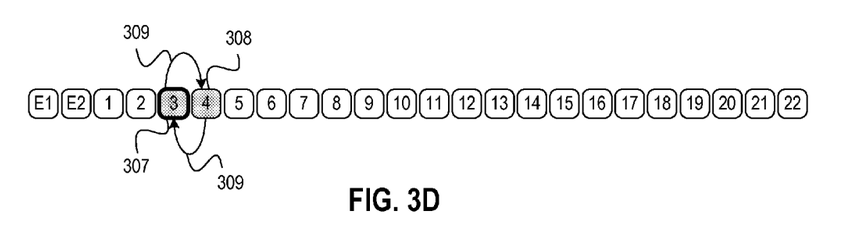
Figure 3E:
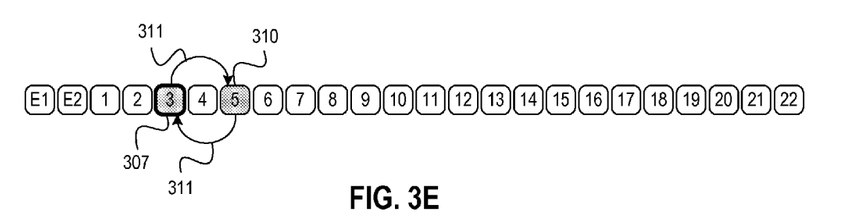
Figure 3F:
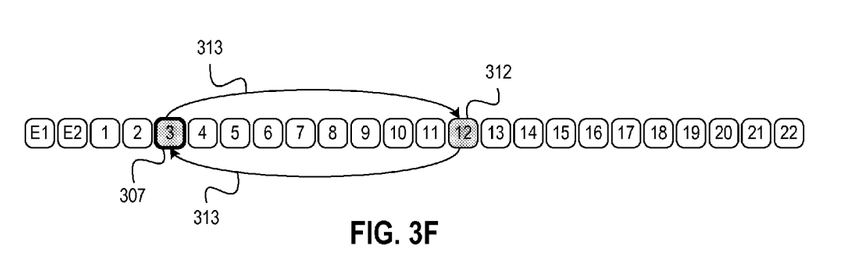

FIGS. 3D-3F show three examples of stimulation channels configured for different types of bipolar stimulation. With bipolar stimulation, the active and reference electrodes of the stimulation channel may both be internal electrodes. The separation between the active and reference internal electrodes may determine the spread of current within the implant recipient's cochlea. A stimulation channel with a shorter distance between the active and reference electrodes may require higher current to produce a corresponding threshold level and/or comfort level than a stimulation channel with a longer distance between the active and reference electrodes in part because the stimulation channel with the shorter distance between the active and reference electrodes may be stimulating a smaller amount of neural tissue. Bipolar stimulation may typically be used for electrical stimulation signals encoded according to the Spectral Peak encoding format.

FIG. 3D shows an example of two electrodes configured for bipolar stimulation on a stimulation channel. For a stimulation channel configured for bipolar stimulation, current flows between an internal active electrode and an internal reference electrode, where the internal reference electrode is adjacent to the internal active electrode. In the example shown in FIG. 3D, the stimulation channel includes active electrode 307 and reference electrode 308, where the active electrode 307 corresponds to internal electrode 3, and the reference electrode corresponds to adjacent internal electrode 4. When the stimulation channel of FIG. 3D is activated, current flows between the active electrode 307 and the reference electrode 308 via path 309.

FIG. 3E shows an example of two electrodes configured for bipolar stimulation BP+1 on a stimulation channel. For a stimulation channel configured for BP+1 stimulation, current flows between an internal active electrode and an internal reference electrode, where the internal reference electrode is located two electrodes away from the internal active electrode. In the example shown in FIG. 3E, the stimulation channel includes active electrode 307 and reference electrode 310, where the active electrode 307 corresponds to internal electrode 3, and the reference electrode corresponds to internal electrode 5. When the stimulation channel of FIG. 3E is activated, current flows between the active electrode 307 and the reference electrode 310 via path 311.

FIG. 3F shows an example of a set of two electrodes configured for bipolar stimulation BP+X on a stimulation channel. For a stimulation channel configured for BP+X stimulation, current flows between an internal active electrode and an internal reference electrode that is X electrodes away from the internal active electrode. In the example shown in FIG. 3F, the stimulation channel is configured for BP+9 stimulation. The stimulation channel shown in FIG. 3F includes active electrode 307 and reference electrode 312, where the active electrode 307 corresponds to internal electrode 3, and the reference electrode 312 corresponds to internal electrode 12. When the stimulation channel of FIG. 3F is activated, current flows between the active electrode 307 to the reference electrode 312 via path 313.

Figure 3G:
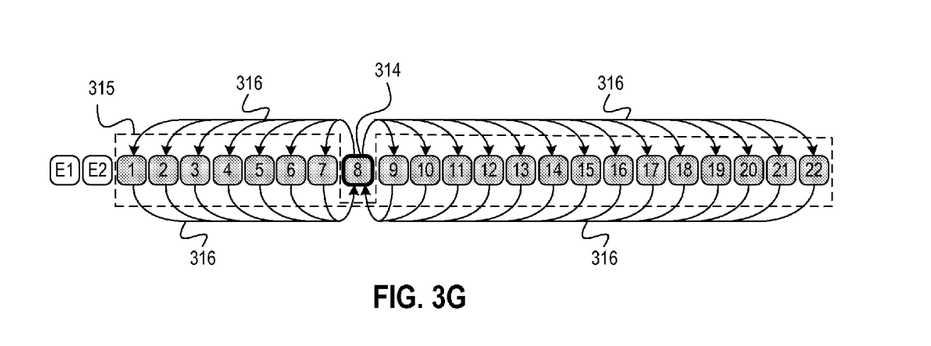

FIG. 3G shows an example of a set of twenty-two electrodes configured for common ground stimulation on a stimulation channel. For a stimulation channel configured for common ground stimulation, current flows between an internal active electrode and all the other internal electrodes of the cochlear implant. The stimulation channel shown in FIG. 3F includes active electrode 314 and the group of twenty one internal reference electrodes 315, where the active electrode 314 corresponds to internal electrode 8, and the group of twenty one internal reference electrodes corresponds to internal electrodes 1-7 and 9-22. When the stimulation channel of FIG. 3G is activated, current flows between the active electrode 308 and the group of twenty one reference electrodes 315 via path 316. Common mode stimulation may typically be used for electrical stimulation signals encoded according to the Spectral Peak format encoding.

In some embodiments, the cochlear implant may be configured so that all the stimulation channels may be configured according to the same type of stimulation mode. In other embodiments, some of the stimulation channels may be configured for one type of stimulation mode while other stimulation channels may be configured for one or more different types of stimulation modes.

3. Stimulation and Response Signals

Figure 4:
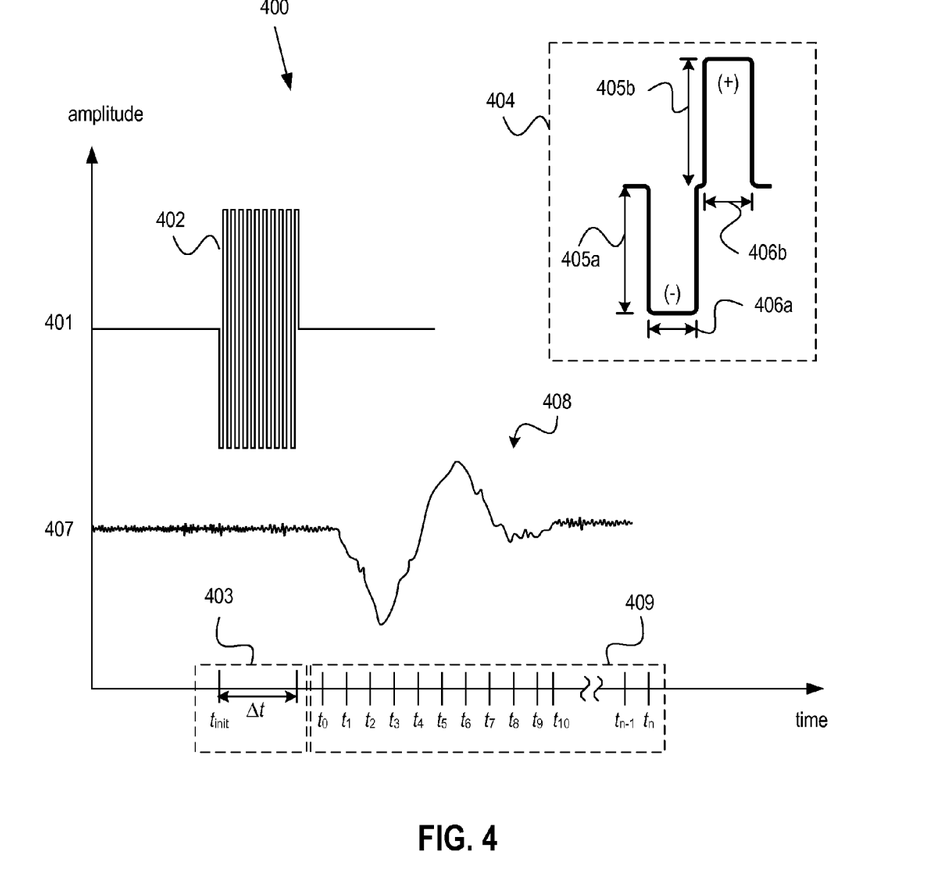
FIG. 4 shows an example of an electrical signal that may be generated by a cochlear implant and a response to the electrical signal that may be measured by the cochlear implant.

FIG. 4 shows an example of an electrical stimulation signal 402 that may be generated by a cochlear implant and a response 408 to the electrical stimulation signal 402 that may be measured by two or more electrodes of the cochlear implant. The graph 400 illustrated in FIG. 4 shows signal amplitude versus time, where signal amplitude is shown on the vertical axis and time is shown on the horizontal axis. Trace 401 corresponds to one stimulation channel of the cochlear implant, and trace 407 corresponds to a signal measured on a recording channel of the cochlear implant. The recording channel may include at least one recording electrode and at least one reference electrode. In some embodiments, the stimulation channel and the recording channel may share one or more electrodes. In further embodiments, the electrodes of the stimulation channel may be different than the electrodes of the recording channel. In operation, a cochlear implant may have multiple stimulation channels configured for delivering electrical stimulation signals to a recipient's cochlea, and any responses to the electrical signal may be measured by two or more electrodes of the cochlear implant, but only one example stimulation channel and only one measured signal are shown in FIG. 4 for illustration.

In some embodiments, the active electrode configured to generate the stimulation signal 402 may be the same electrode configured to measure the response 408. In other embodiments, the active electrode configured to generate the stimulation signal 402 may be one of a group of electrodes configured to measure the response 408. In still other embodiments, the active electrode configured to generate the stimulation signal 402 may be a different electrode than the two or more electrodes configured to measure the response 408.

3.1 Stimulation Signal Generation

Trace 401 on graph 400 corresponds to one stimulation channel of a cochlear implant. The stimulation mode of the stimulation channel may correspond to any of the stimulation modes described herein with respect to FIGS. 3A-3G. At time $t_{init}$, the cochlear implant may generate a stimulation signal 402 for some duration, $\Delta t$, as shown along the horizontal axis of graph 400 in box 403. The stimulation signal 402 may include one or more current pulses. The stimulation signal 402 shown in FIG. 4 is a group of substantially square wave pulses, but other types of waveforms could be used as well.

An expanded view of one current pulse 404 of the stimulation signal 402 is shown in the inset. The current pulse 404 of the stimulation signal 402 shown here is a charge-balanced, biphasic current pulse having an amplitude and pulse width. In some embodiments, the biphasic current pulse may also have a phase gap between the positive and negative phases of the pulse. The amplitude $405a$ and pulse width $406a$ of the negative phase of the current pulse 404 are substantially the same as the amplitude $405b$ and pulse width $406b$ of the positive phase of the current pulse 404. As a result, the electrical stimulus delivered to a nerve in the positive phase of the current pulse may be substantially the same as the electrical stimulus delivered to the nerve in the negative phase of the current pulse so that substantially no net charge remains after the completion of an individual current pulse. The stimulation signal 402 may include multiple biphasic current pulses that may be similar to the biphasic current pulse 404.

In the biphasic current pulse 404 shown in FIG. 4, the amplitude 405 may correspond to a level of electrical current delivered via the stimulation channel 401. In some embodiments, the current level may represent the amplitude of the biphasic current pulse in microamperes (µA). In some embodiments, the amplitude range may be substantially from about 10 µA to about 1.75 mA (or 1750 µA), but other ranges may be used in other embodiments. The pulse width 406 may correspond to the amount of time that the current is applied via the stimulation channel 401, expressed in microseconds (µs) per phase of the biphasic current pulse 404.

A charge per phase of the biphasic current pulse 404 may be calculated by multiplying the amplitude 405 of the biphasic current pulse 404 by the pulse width 406 of the biphasic current pulse 404. A biphasic current pulse with a higher charge per phase may cause the recipient to experience a louder sound sensation than a biphasic pulse with a lower charge per phase. Because the charge per phase is the product of the amplitude and pulse width, increasing either the amplitude or the pulse width of a biphasic current pulse may cause the recipient to experience a louder sound sensation, and decreasing either the amplitude or the pulse width of the biphasic current pulse may cause the recipient to experience a softer sound sensation.

3.2 Response Signal Measurement

As mentioned above, at time $t_{init}$, the cochlear implant may generate the stimulation signal 402 for some duration, Δt, as shown along the x-axis of graph 400 in box 403. In some embodiments, shortly after the end of the stimulation signal 402, at least two electrodes of the cochlear implant may be used to measure the response 408 to the stimulation signal 402. In other embodiments, the response 408 may start while the stimulation signal 402 is still active, and in such embodiments, the at least two electrodes of the cochlear implant may measure the response 408 to the stimulation signal 402 while the stimulation signal 402 is still active. Whether the response 408 begins during the stimulation signal 402 or after the stimulation signal 402 is inactive may depend on the duration of the stimulation signal 402.

In some embodiments, measuring the response 408 may be accomplished by sampling the signal 407 at an electrode configured to measure the response 408. In some embodiments, the response 408 may be sampled at regular intervals during a sampling window 409. The sampling window 409 may include a plurality of n sample periods beginning at time $t_0$ and ending at time $t_n$. For example, in the sample window 409 shown in FIG. 4, the first sample period may be from time $t_0$ until time $t_1$, the second sample period may be from time $t_1$ to time $t_2$, etc. In some embodiments, the sample periods may be configurable and/or variable. In other embodiments, the sample periods may be fixed. In some embodiments, the sampling window 409 may be configurable and/or variable. In other embodiments, the sampling window 409 may be fixed.

Samples of the response 408 collected during the sample window 409 may be collected by the signal measurement module 224 (FIG. 2A) for signal analysis. The samples may be analyzed by circuitry and/or one or more processors in at least one of the signal measurement module 224 (FIG. 2A), the processor module 202 (FIG. 2A), the fitting system 145 (FIGS. 1A and 1B), and/or another external computing device configured to analyze the response 408 and to determine whether the measured response 408 includes at least one non-auditory nerve stimulation.

3.3 Response Signal Analysis

Determining whether a non-auditory nerve stimulation is present in the response 408 may include analyzing one or more signal characteristics of the sampled response 408 to determine whether the one or more signal characteristics of the response 408 are indicative of a particular non-auditory nerve stimulation. For example, one or more signal characteristics of the response 408, such as the voltage, voltage change over time, rate of change of the voltage over time, amperage, amperage change over time, rate of change of the amperage over time, frequency, frequency variation over time, rate of change of the frequency variation over time, impedance, impedance change over time, rate of change of impedance over time, and/or the duration of the response 408 may be analyzed to determine whether the response 408 may have included a non-auditory nerve stimulation.

In some embodiments, one or more signal characteristics of the response 408 can be compared to one or more model signal characteristics of a particular type of non-auditory nerve stimulation. In these embodiments, one or more substantial similarities between one or more signal characteristics of the response 408 and one or more model signal characteristics of the particular non-auditory nerve stimulation may suggest that the particular non-auditory nerve stimulation is present in the response 408. In some embodiments, the non-auditory nerve stimulation may be a facial nerve stimulation, and the one or more signal characteristics may be based on voltage, amperage, impedance, frequency, and/or duration, as described above.

For situations where the beginning of the response 408 may overlap with the stimulation signal 402 in time, or for situations when artifacts of the stimulation signal 402 may be present in the response 408, determining whether the response 408 includes a non-auditory nerve stimulation may include subtracting one or more signal components corresponding to the stimulation signal 402 and/or stimulation signal artifacts from the response 408 to obtain a better representation of the response 408 with less interference from the stimulation signal 402 and/or the stimulation signal artifacts. Similarly, in some embodiments, if one or more signal characteristics of a recipient's auditory nerve response are known, then one or more corresponding signal characteristics of the response 408 can be compared to the one or more known signal characteristics of the recipient's auditory nerve response, and differences between the signal characteristics of the response 408 and the signal characteristics of the known auditory nerve response might suggest that a non-auditory nerve stimulation is present in the response 408. For example, in some embodiments, determining whether the response 408 includes a non-auditory nerve stimulation may therefore include (i) subtracting one or more components corresponding to the simulation signal 402, stimulation signal artifacts, and/or a known auditory nerve stimulation from the response 408, and (ii) analyzing the differences between the components of the response 408 and the components of the stimulation signal 402, stimulation signal artifacts, and/or a known auditory nerve stimulation.

Additionally, or alternatively, in some embodiments, one or more signal characteristics of the response 408 may be compared to one or more reference signal characteristics, and one or more similarities between the signal characteristics of the response 408 and the reference signal might suggest that a non-auditory nerve stimulation is present in the response 408. Similarly, one or more signal characteristics of the response 408 may be compared to one or more corresponding thresholds, and one or more signal characteristics of the response 408 exceeding at least one corresponding threshold may suggest that a non-auditory nerve stimulation is present in the response 408.

For some embodiments, determining whether the response 403 includes a non-auditory nerve stimulation may include any combination of two or more of the above-described signal analysis techniques. For example, in some embodiments, one or more components of the stimulation signal 402 may be subtracted from one or more components of the response 408 to obtain a better representation of the response 408 with less interference from the stimulation signal 402. Then, signal components of the representation of the response 408 may be compared to model signal components of a facial nerve stimulation, where one or more similarities between the signal components may suggest that the response 408 included a facial nerve stimulation.

In some embodiments, an expert system may be used to determine whether the response 408 contains a non-auditory nerve stimulation. Expert systems may include algorithms configured to recognize patterns based on classifications performed by a human expert of the pattern domain. Co-pending U.S. application Ser. No. 10/569,054, filed Dec. 25, 2008, titled "Automatic Determination of the Threshold of an Evoked Neural Response," and incorporated herein by reference, describes various systems and methods that use recognition algorithms to determine whether a measured signal contains a neural response. Systems and methods similar to those described in the Ser. No. 10/569,054 application can be modified to detect a non-auditory nerve stimulation by configuring a recognition algorithm based on a set of sample response signals, wherein some of the sample response signals contain a non-auditory nerve stimulation and some of the sample response signals do not contain a non-auditory nerve stimulation.

In some embodiments, one or more configuration settings of the cochlear implant may be changed in response to determining that a non-auditory nerve stimulation was present in the response 408. For example, the threshold levels and/or comfort levels of the stimulation channel may be changed. Additionally, or alternatively, the stimulation channel may be changed to a different stimulation mode (e.g., any of the stimulation modes shown and described with respect to FIGS. 3A-G), the amplitude 405 of the biphasic current pulses of the stimulation signal may be increased or reduced, the pulse width 406 of the biphasic pulses of the stimulation signal may be increased or reduced, and/or the stimulation rate of the biphasic current pulses of the stimulation channel may be increased or reduced. In some instances, a particular electrode may be disabled so that it is not available for use as an active and/or reference electrode for a stimulation channel.

4. Example Methods for Signal Generation, Measurement, and Analysis

Figure 5:
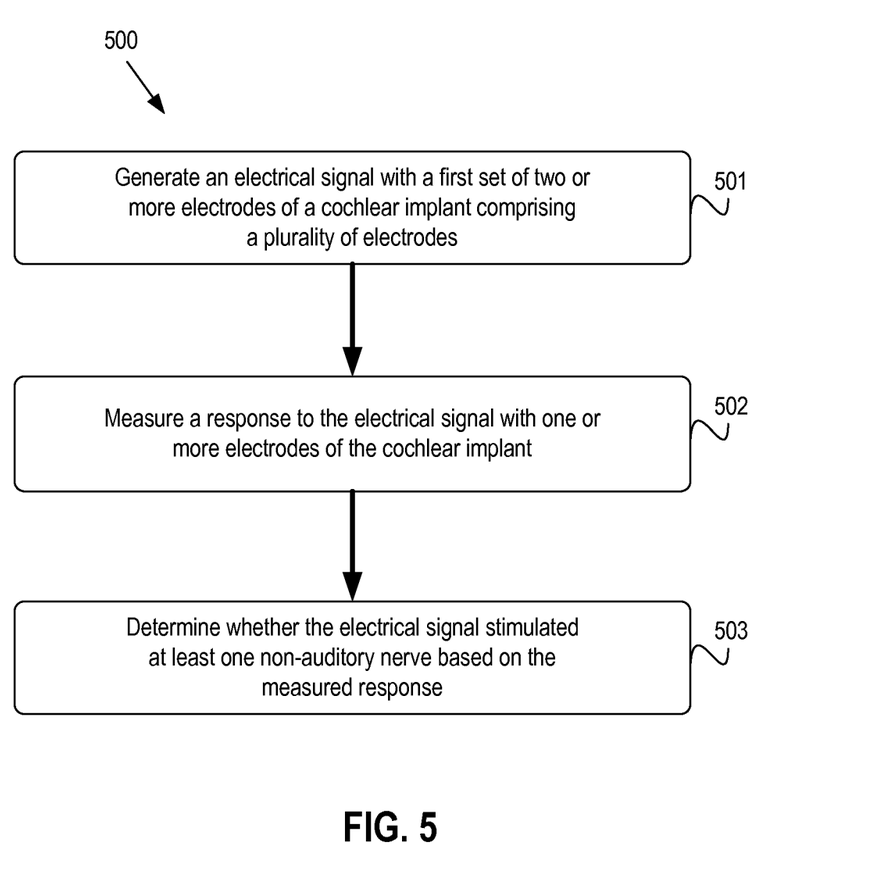
FIG. 5 shows a method for determining whether an electrical signal stimulated at least one non-auditory nerve of a cochlear implant recipient according to some example embodiments.

FIG. 5 shows a method 500 for determining whether an electrical signal generated by a cochlear implant stimulated at least one non-auditory nerve of a cochlear implant recipient according to some example embodiments. In some embodiments, the cochlear implant may be an implant such as implant 100 (FIG. 1A), implant 200 (FIG. 2A), or any of the implants disclosed and/or described in U.S. Pat. Nos. 4,532,930, 6,537,200, 6,565,503, 6,575,894 and 6,697,674, for example.

At step 501, an electric signal is generated with a cochlear implant. The cochlear implant may include a plurality of electrodes, such as, for example, the external electrodes 207 (FIG. 2A) and/or the internal electrodes 209 (FIG. 2A). In some embodiments, a first set of two more electrodes of the plurality of electrodes may be used to generate the electric signal. In some embodiments, the electric signal may be similar to any of the stimulation signals described herein, such as, for example, the stimulation signal 402 (FIG. 4), and the first set of two or more electrodes may correspond to the various groupings of electrodes and stimulation mode configurations described herein with respect to FIGS. 3A-G.

At step 502, a response to the electrical signal may be measured using two or more electrodes of the cochlear implant. The measured response may be similar to response 408 (FIG. 4). Measuring the response may include measuring and/or analyzing one or more signal components related to the response's voltage, amperage, frequency, and/or duration, such as, for example, the signal components described herein with respect to FIG. 4. In some embodiments, the cochlear implant may use the same set of electrodes for generating the electrical signal and for measuring the response. In other embodiments, the cochlear implant may use different electrodes for generating the electrical signal and for measuring the response.

Step 503 includes determining whether the electrical signal stimulated at least one non-auditory nerve based on the measured response. In some embodiments, the cochlear implant may be configured to determine whether the electrical signal stimulated at least one non-auditory nerve. For example, circuitry and/or one or more processors of any of the signal measurement module 224 (FIG. 2B), processor module 202 (FIG. 2A), and/or other modules of the cochlear implant described in FIGS. 2A-B, alone or in combination, may be configured to analyze the measured response and to determine whether the response included a non-auditory nerve stimulation. In other embodiments, the measured signal may be sent to a cochlear implant fitting system 145 (FIGS. 1A-B) and/or one or more external computing devices configured to analyze the measured response and to determine whether the response included a non-auditory nerve stimulation.

Some embodiments may also include alerting a cochlear implant recipient and/or an audiologist that a non-auditory nerve stimulation has been detected. Also, some embodiments may additionally and/or alternatively include changing one or more configuration settings of the cochlear implant in response to determining whether the electrical signal stimulated at least one non-auditory nerve. For example, changing one or more configuration settings may include at least one of (i) changing at least one threshold level and/or comfort level of a stimulation channel; (ii) changing the stimulation mode of a stimulation channel; (iii) changing at least one of the amplitude, pulse width, and/or stimulation rate of the stimulation signal sent via the stimulation channel; and/or (iv) disabling at least one electrode so that it is not available for use as an active and/or reference electrode for a stimulation channel.

5. Example Algorithms for Use with Cochlear Implants

Figure 6:
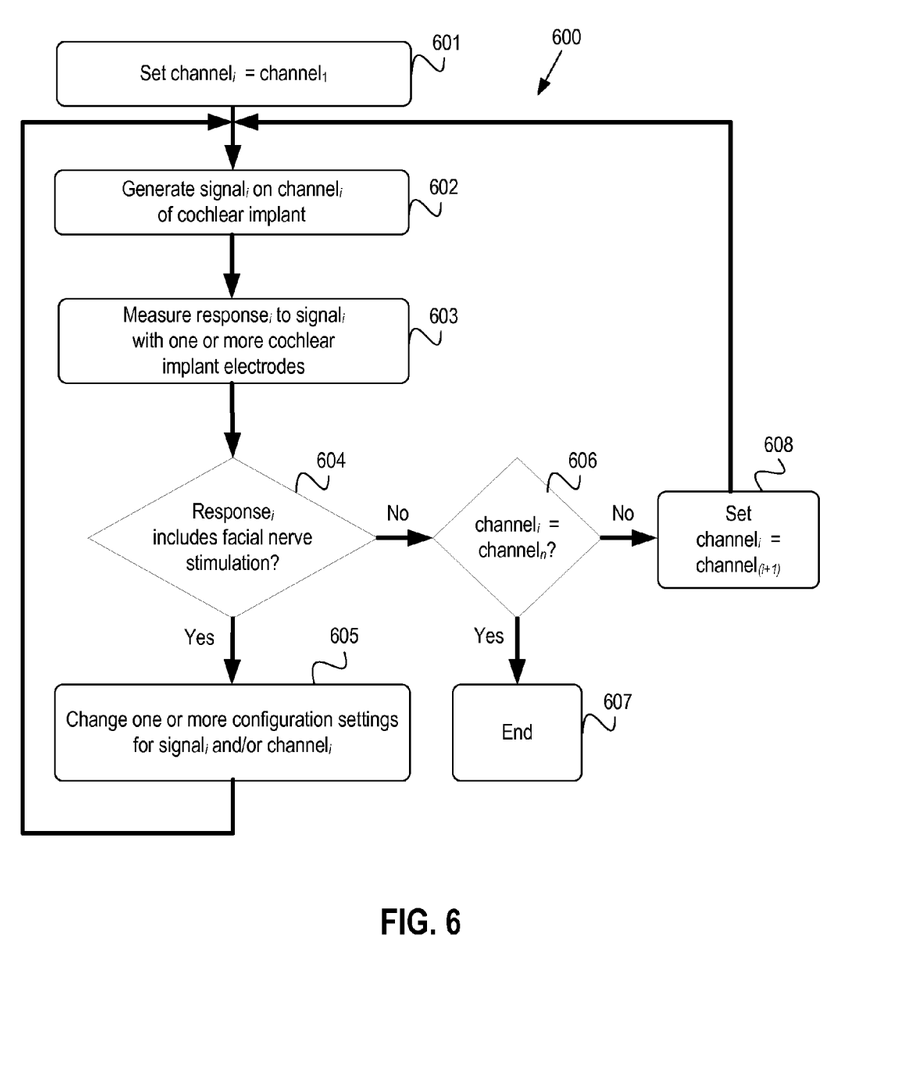
FIG. 6 shows an example algorithm for determining whether electrical signals of a group of n stimulation channels of a cochlear implant stimulated a facial nerve of a cochlear implant recipient according to some example embodiments.

FIG. 6 shows an example algorithm for determining whether electrical signals of a group of n stimulation channels of a cochlear implant stimulated a facial nerve of a cochlear implant recipient according to some example embodiments.

The algorithm 600 begins at step 601, where the stimulation channel$_i$ is set to the first stimulation channel (i.e., stimulation channel$_1$) of a plurality of n stimulation channels of the cochlear implant. At step 602, the stimulation signal$_i$ is generated on the stimulation channel$_i$ of the cochlear implant. In some embodiments, the stimulation signal$_i$ may be a signal similar to the stimulation signal 402 (FIG. 4).

At step 603, a response$_i$ to the stimulation signal$_i$ is measured with two or more electrodes of the cochlear implant. The response$_i$ may be similar to the response 408 (FIG. 4). The response$_i$ may be measured according to any of the measurement procedures described herein. At step 604, a determination of whether the response$_i$ included a facial nerve stimulation is made. Whether the response$_i$ included a facial nerve stimulation can be determined by or according to any of the systems and/or methods described herein.

If it is determined that the response$_i$ includes a facial nerve stimulation, then, at step 605, one or more configuration settings for the stimulation signal$_i$ and/or the stimulation channel$_i$ may be changed. For example, changing one or more configuration settings for the stimulation signal$_i$ and/or the stimulation channel$_i$ may include at least one of: (i) changing the threshold level and/or comfort level of the stimulation channel$_i$; (ii) changing the stimulation mode of the stimulation channel$_i$; and/or (iii) changing the amplitude, pulse width, and/or stimulation rate of the stimulation signal$_i$ sent via the stimulation channel$_i$.

After changing one or more configuration settings for the stimulation signal$_i$ and/or the stimulation channel$_i$ at step 605, the algorithm 600 returns to step 602, where the modified stimulation signal$_i$ is generated on the stimulation channel$_i$ of the cochlear implant. At step 603, a response$_i$ to the modified stimulation signal$_i$ is measured with two or more electrodes of the cochlear implant, and at step 604, a determination of whether the response$_i$ included a facial nerve stimulation is made. If it is determined at step 604 that the response$_i$ included a facial nerve stimulation, then further changes to the configuration settings for stimulation signal$_i$ and/or stimulation channel$_i$ may be made at step 605. If it is determined at step 604 that the response$_i$ included a facial nerve stimulation after multiple iterations of steps 602-605 for the stimulation signal$_i$ and the stimulation channel$_i$, then step 605 may also include disabling the active electrode of the stimulation channel$_i$.

If it is determined at step 604 that the response$_i$ does not include a facial nerve stimulation, then the algorithm 600 may proceed to step 606. At step 606, a determination is made as to whether the stimulation channel$_i$ is the last stimulation channel$_n$ of the n stimulation channels of the cochlear implant. If the stimulation channel$_i$ is the last stimulation channel$_n$, then the algorithm 600 may end at step 607. But if the stimulation channel$_i$ is not the last stimulation channel$_n$, then the stimulation channel$_i$ may be set to stimulation channel$_{(i+1)}$ (i.e., the next stimulation channel of the n stimulation channels) at step 608. Then, the algorithm 600 returns to step 602 to start the process again with the next stimulation channel (i.e., stimulation channel$_{(i+1)}$).

The algorithm 600 may be performed during the process of initially fitting the cochlear implant to the recipient shortly after the cochlear implant has been implanted in the recipient's cochlea. Alternatively, or additionally, algorithm 600 may also be performed one or more times after the initial fitting as needed or desired.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
   delivering, with a first set of electrodes of a cochlear implant, an electrical signal to a cochlea of a recipient of the cochlear implant, wherein the cochlear implant comprises a plurality of electrodes, and wherein at least a portion of the plurality of electrodes are positioned within the cochlea of the recipient to stimulate an auditory nerve of the recipient;
   measuring, with a second set of electrodes of the cochlear implant, a response to the electrical signal; and
   based on the measured response, determining that the electrical signal directly and electrically stimulated a facial nerve of the recipient.

2. The method of claim 1, wherein determining that the electrical signal directly and electrically stimulated the facial nerve of the recipient comprises:
   comparing one or more signal characteristics of the response to one or more model signal characteristics of facial nerve stimulation to identify one or more similarities between the one or more signal characteristics of the response and the one or more model signal characteristics of the facial nerve stimulation; and
   analyzing one or more similarities between the one or more signal characteristics of the response and the one or more model signal characteristics of the facial nerve stimulation.

3. The method of claim 1, wherein the measuring of the response overlaps with the delivering of the electrical signal to the cochlea, and wherein the method further comprises:
   prior to determining that the electrical signal directly and electrically stimulated the facial nerve of the recipient, subtracting one or more signal components corresponding to the electrical signal or stimulation signal artifacts from the response.

4. The method of claim 1, wherein one or more signal characteristics of a recipient's auditory nerve response are known, and wherein determining that the electrical signal directly and electrically stimulated the facial nerve of the recipient comprises:
   comparing signal characteristics of the response to the one or more known signal characteristics of the recipient's auditory nerve response to identify one or more differences between the signal characteristics of the response and the one or more known signal characteristics of the recipient's auditory nerve response; and
   analyzing the one or more differences between the signal characteristics of the response and the one or more known signal characteristics of the recipient's auditory response.

5. The method of claim 1, wherein determining that the electrical signal directly and electrically stimulated the facial nerve of the recipient comprises:
   comparing signal characteristics of the response to one or more corresponding thresholds; and
   determining that one or more signal characteristics of the response exceed at least one corresponding threshold.

6. The method of claim 1, wherein the cochlear implant has a plurality of configuration settings, and wherein the method further comprises:
   in response to determining that the electrical signal directly and electrically stimulated the facial nerve, changing one or more configuration settings of the cochlear implant such that delivery of the electrical signal with the first set of electrodes does not directly and electrically stimulate the facial nerve.

7. The method of claim 1, further comprising sending the measured response to a computing device configured to determine that the electrical signal directly and electrically stimulated the facial nerve.

8. The method of claim 7, further comprising generating an alert in response to determining that the electrical signal directly and electrically stimulated the facial nerve.

9. The method of claim 1, further comprising:
in response to determining that the electrical signal directly and electrically stimulated the facial nerve, changing one or more of an amplitude, a pulse width, or a pulse rate of the electrical signal such that delivery of the electrical signal with the first set of electrodes does not directly and electrically stimulate the facial nerve.

10. The method of claim 1, wherein the first set of electrodes comprises an active electrode and a reference electrode, and wherein the method further comprises:
changing at least one of the active electrode or the reference electrode to a different electrode in the plurality of electrodes in response to determining that the electrical signal directly and electrically stimulated the facial nerve.

11. The method of claim 1, wherein the first set of electrodes comprises an active electrode and a reference electrode, and wherein the method further comprises:
disabling the active electrode in response to determining that the electrical signal directly and electrically stimulated the facial nerve.

12. The method of claim 1, wherein measuring the response to the electrical signal comprises measuring at least one of a current, a voltage, a frequency, or an impedance with the second set of electrodes of the cochlear implant.

13. The method of claim 1, wherein determining whether the first electrical signal stimulated the facial nerve comprises analyzing the measured response with a recognition algorithm implemented in at least one of software, hardware, or firmware.

14. A cochlear implant comprising:
a plurality of electrodes including (i) a first set of electrodes configured to deliver at least one electrical signal to a cochlea of recipient of the cochlear implant to stimulate the recipient's auditory nerve, and (ii) a second set of electrodes configured to measure a response to delivery of the at least one electrical signal to the cochlea; and
circuitry configured to analyze the measured response and determine, based on the analysis, that the at least one electrical signal directly and electrically stimulated a facial nerve of the recipient.

15. The cochlear implant of claim 14, further comprising:
non-transitory machine-readable storage media configured to store a plurality of configuration settings for the cochlear implant, wherein in response to determining that the electrical signal directly and electrically stimulated the facial nerve, the cochlear implant is configured to change one or more of the configuration settings of the cochlear implant such that delivery of the electrical signal with the first set of electrodes does not directly and electrically stimulate the facial nerve.

16. The implant of claim 14, wherein the implant is further configured to change one or more of an amplitude, a pulse width, or a stimulation rate of the electrical signal in response to determining that the electrical signal directly and electrically stimulated the facial nerve.

17. The cochlear implant of claim 14, wherein the first set of electrodes comprises an active electrode and a reference electrode, and wherein the cochlear implant further comprises circuitry configured to change at least one of the active electrode or the reference electrode to a different electrode in the plurality of electrodes in response to determining that the electrical signal directly and electrically stimulated the facial nerve.

18. The cochlear implant of claim 14, wherein the first set of electrodes comprises an active electrode and a reference electrode, and wherein the implant further comprises circuitry configured to disable the active electrode in response to determining that the electrical signal directly and electrically stimulated the facial nerve.

19. The cochlear implant of claim 14, further comprising a component configured to analyze the measured response with a recognition algorithm implemented in at least one of software, hardware, or firmware.

20. The cochlear implant of claim 14, wherein to analyze the measured response and determine that the electrical signal directly and electrically stimulated the facial nerve of the recipient, the circuitry is configured to:
compare one or more signal characteristics of the response to one or more model signal characteristics of facial nerve stimulation to identify one or more similarities between the one or more signal characteristics of the response and the one or more model signal characteristics of the facial nerve stimulation; and
analyze one or more similarities between the one or more signal characteristics of the response and the one or more model signal characteristics of the facial nerve stimulation.

21. A system comprising: a computing device configured to communicate with a cochlear implant, wherein the computing device is configured to: receive, from the cochlear implant, a measured response to an electrical signal applied via a first set of electrodes of the cochlear implant, wherein the electrical signal is applied to stimulate a recipient's auditory nerve and wherein the measured response is measured via a second set of electrodes of the cochlear implant; and analyze the measured response and determine that the measured response includes an indication that the electrical signal directly and electrically stimulated a facial nerve of the implant recipient.

22. The system of claim 21, wherein the computing device is further configured to generate an alert in response to determining that the measured response includes the indication that the electrical signal directly and electrically stimulated the facial nerve of the implant recipient.

23. The system of claim 21, wherein the implant has a plurality of configuration settings, and wherein in response to determining that the electrical signal directly and electrically stimulated the facial nerve the computing device is configured to send instructions to the implant to change one or more of an amplitude, a pulse width, or a stimulation rate of the electrical signal.

24. The system of claim 21, wherein the first set of electrodes includes an active electrode and a reference electrode, and wherein in response to determining that the electrical signal directly and electrically stimulated the facial nerve the computing device is further configured to send instructions to the implant to change at least one of the active electrode or the reference electrode to a different electrode in the plurality of electrodes.

25. The system of claim 21, wherein the first set of electrodes comprises an active electrode and a reference electrode, and wherein in response to determining that the electrical signal directly and electrically stimulated the facial nerve the computing device is further configured to send instructions to the implant to disable the electrode in response.

26. The system of claim 21, wherein the computing device is configured to analyze the received measured response with a recognition algorithm implemented in at least one of software, hardware, or firmware.

* * * * *